United States Patent [19]

Hess et al.

[11] 4,074,044

[45] Feb. 14, 1978

[54] CYANOPROSTAGLANDINS

[75] Inventors: Hans-Jurgen E. Hess; Thomas K. Schaaf, both of Old Lyme, Conn.

[73] Assignee: Pfizer Inc., New York, N.Y.

[21] Appl. No.: 790,234

[22] Filed: Apr. 25, 1977

Related U.S. Application Data

[62] Division of Ser. No. 712,361, Aug. 6, 1976, Pat. No. 4,045,465.

[51] Int. Cl.$^2$ .................. C07C 177/00; C07D 309/10
[52] U.S. Cl. .................................. 542/402; 542/426; 542/447
[58] Field of Search ............................ 260/240 R, 464

[56] References Cited

U.S. PATENT DOCUMENTS

| | | | |
|---|---|---|---|
| 3,723,423 | 3/1973 | Anderson et al. | 260/240 R |
| 3,853,854 | 12/1974 | Weinshenker et al. | 260/240 R |
| 3,870,747 | 3/1975 | Wendler et al. | 260/464 X |
| 3,923,872 | 12/1975 | Caton et al. | 260/464 X |

OTHER PUBLICATIONS

J. Am. Chem. Soc. 90:12; 6/5/1968 — "Total Synthesis of Prostaglandins . . ." pp. 3245-3247.

*Primary Examiner*—Allen B. Curtis
*Attorney, Agent, or Firm*—Connolly and Hutz

[57] ABSTRACT

The 19-cyano-20-nor derivatives of prostaglandins $E_1$ and $E_2$, and certain esters thereof, are bronchodilatory agents, useful in the treatment of bronchial asthma, bronchitis, pneumonia and emphysema. The 19-cyano-20-nor derivatives of prostaglandins $E_1$ and $E_2$, and certain esters thereof, which also have protecting groups on the hydroxy groups at C-11 and C-15 are useful intermediates for the preparation of the bronchodilatory agents of this invention.

3 Claims, No Drawings

CYANOPROSTAGLANDINS

CROSS-REFERENCE TO RELATED APPLICATION

This application is a division of application Ser. No. 712,361 filed Aug. 6, 1976 now U.S. Pat. No. 4,045,465.

BACKGROUND OF THE INVENTION

This invention relates to certain new chemical compounds. More particularly it relates to certain chemical compounds which have valuable medicinal properties, and which are new members of the class of compounds known as the prostaglandins.

The prostaglandins are derivatives of the C-20 fatty acid 7-(2β-octylcyclopent-1α-yl)heptanoic acid, which is also known as prostanoic acid and is depicted as follows:

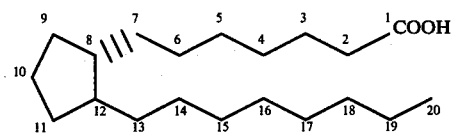

Prostaglandins exist naturally and they have been isolated from a variety of mammalian sources. Natural prostaglandins of the so-called "E-series" have an oxo group at C-9, a hydroxy group at C-11 trans to the adjacent eight-carbon side chain at C-12, and an α-hydroxy group at C-15. Individual members of the E-series of prostaglandins can be further characterized by the number and location of double bonds in the C-8 and C-12 side chains. For example, prostaglandin $E_1$ has a 13-14 trans double bond, and prostaglandin $E_2$ has a 13-14 trans double bond and a 5-6 cis double bond. Prostaglandin $E_2$ is also named as 9-oxo-11α,15α-dihydroxy-cis-5-trans-13-prosta-5,13-dienoic acid, and it has the following structure:

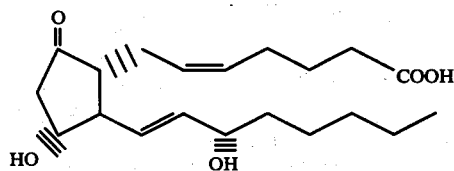

Prostaglandins of the E-series cause a wide variety of biological and pharmacological responses, both in vitro and in vivo. For example, E-series prostaglandins stimulate uterine smooth muscle, have hypotensive, diuretic, bronchodilatory and antilipolytic activities, and also have effects on blood platelet aggregation and gastric acid secretion. (See further: Bergstrom et al., *Pharmacological Reviews*, 20,1(1968) and Caton, *progress in Medicinal Chemistry*, Butterworths Publications, Ltd., London, 1971, Volume 8, page 317). However, in order to increase their medicinal usefulness, it is desirable to have compounds with a greater specificity of action. Accordingly it is an object of this invention to provide certain derivatives of prostaglandins $E_1$ and $E_2$ which have useful bronchodilatory properties, but which have substantially no effect on uterine smooth muscle and reduced hypotensive and gastric antisecretory effects.

SUMMARY OF THE INVENTION

It is the principal object of the present invention to provide novel bronchodilatory prostaglandin compounds of the formula I.

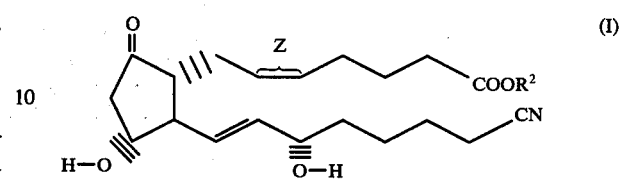

wherein $COOR^2$ represents a free or an esterified carboxy group, and Z represents a single bond or a cis double bond. Typical examples of esterified carboxy groups are those wherein $R^2$ is lower-alkyl, phenyl, substituted phenyl, benzyl, substituted benzyl, cyclopentyl, cyclohexyl, and the like. However, the preferred bronchodilatory compounds of this invention are those wherein $R^2$ is selected from the group consisting of hydrogen, alkyl having from one to four carbon atoms and 4-biphenylyl.

It is a further object of this invention to provide novel prostaglandin compounds of the formula IA, wherein $R^2$ and Z are as defined previously, and $R^1$ is a hydroxy protecting group which can be removed easily under mildly acidic conditions. Typical examples of hydroxy protecting groups which can be used for $R^1$ are 2-tetrahydropyranyl, 2-tetrahydrofuranyl and dimethyl-t-butylsilyl.

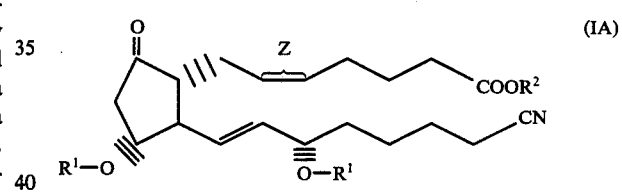

Said compounds of the formula IA are useful as intermediates for preparing the said compounds of the formula I.

A still further object of this invention is to provide a method for alleviating bronchial constriction and improving nasal patency in mammals, particularly humans, requiring such treatment.

DETAILED DESCRIPTION OF THE INVENTION

The compounds of this invention are the compounds of formulae I and IA and, as will be appreciated by one skilled in the art, the compounds of I and IA possess several centers of asymmetry (asymmetrically-substituted carbon atoms). Throughout this specification, broken line attachment of a substituent to the cyclopentane ring of a compound of formula I or IA, and all other cyclopentane derivatives, is intended to indicate that the substituent is below the plane of the cyclopentane ring. Such attachment is also referred to as the alpha configuration (α-configuration). Conversely, solid line attachment of a substituent to the cyclopentane ring of the cyclopentane compounds in this specification is intended to indicate attachment of that substituent above the plane of the 5-membered ring. This latter attachment is also called the beta configuration (β-configuration). As written above, therefore, a compound of formula I or IA represents a single isomer, and it represents a single isomer having absolute configurations (absolute stereochemistries) at positions 8, 11 and 12, respectively, corresponding to those at positions 8, 11 and 12, respectively, of the naturally-occurring prostaglandins of the E group (e.g. $PGE_1$ and $PGE_2$) obtained from mammalian tissues. Additionally, broken line attachment of the $OR^1$ or OH substituent to C-15 in a compound of the formula I or IA indicates that C-15 has the (S)-configuration (i.e. the $OR^1$ or OH group is in the α-configuration according to common prostaglandin stereochemical notation).

Throughout this specification, "THP" represents 2-tetrahydropyranyl.

In one method according to the invention, the compound of the formula I, wherein $R^2$ is hydrogen and Z represents a cis double bond, is prepared by the method shown in Scheme A.

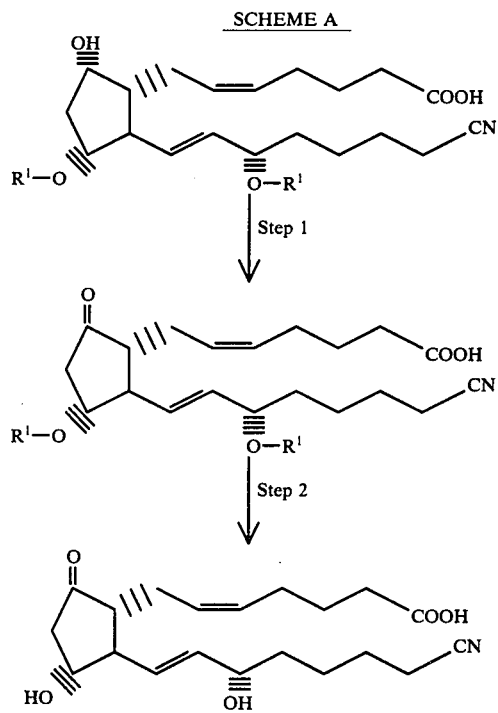

According to Scheme A, the compound of the formula II is first oxidized to the corresponding compound III. Although a variety of oxidizing agents known in the art for oxidizing secondary alcohols to ketones can be used, a particularly convenient reagent is chromic acid in acetone (the Jones reagent). In a typical procedure, a solution of the compound of the formula II in acetone is treated with approximately the stoichiometric amount of the oxidant, at about 0° to about −20° C. The reaction is complete within about 5 minutes to 1 hour. Any excess oxidant is then decomposed, for example using isopropanol, and the product is isolated by the usual procedure of solvent extraction.

In step 2 of Scheme A, the hydroxy protecting groups are removed from the compound of the formula III, to give the compound of formula I, wherein $R^2$ is hydrogen and Z represents a cis double bond. The protecting groups are removed by treating the compound of the formula III with acid, under mild conditions. When $R^1$ is 2-tetrahydropyranyl, 2-tetrahydrofuranyl or dimethyl-t-butylsilyl, a convenient way of removing these groups involves treating the compound of the formula III with aqueous acetic acid at or about 25° C. The reaction usually takes several hours substantially to reach completion, e.g. from about 10 to about 40 hours.

In one method according to the invention, the compound of the formula I, wherein $R^2$ is hydrogen and Z represents a single bond, is prepared by the method shown in Scheme B:

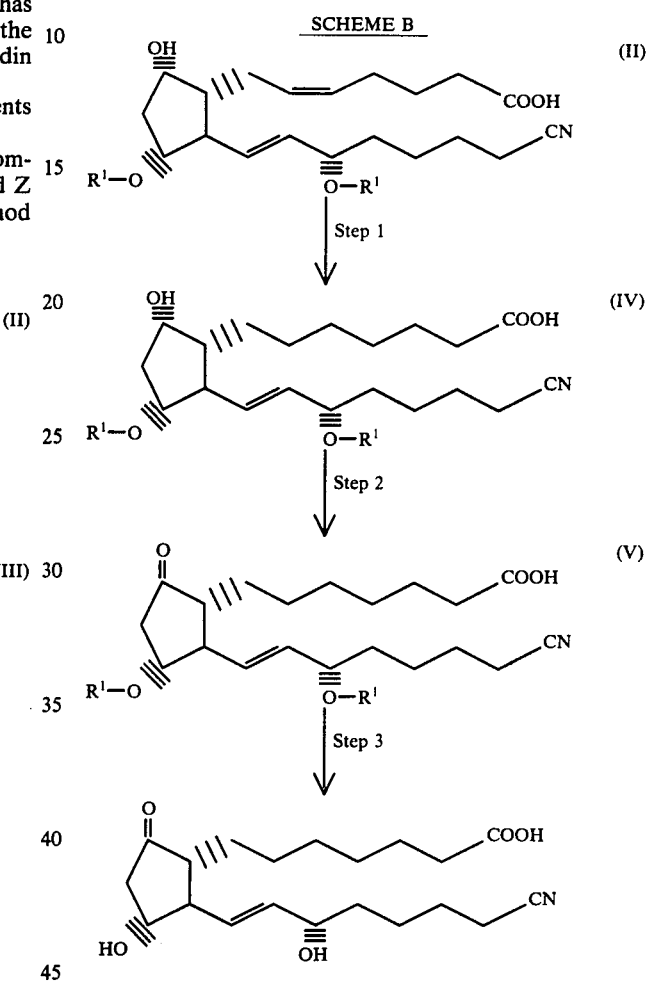

Step 1 of Scheme B is a conventional hydrogenation reaction, and it is usually carried out by stirring or shaking a solution of the compound of the formula II under an atmosphere of hydrogen, or hydrogen mixed with an inert diluent such as nitrogen or argon, in the presence of a catalytic amount of an appropriate metal catalyst. Typical metal catalysts which can be used are rhodium, palladium and platinum, with the preferred agent being palladium. Convenient solvents are lower alkanols such as methanol and ethanol, ethers such as diethyl ether and tetrahydrofuran and low molecular weight esters such as ethyl acetate and butyl acetate. The hydrogenation is usually conducted at or about atmospheric pressure, and at or about −20° C. The palladium catalyst is conveniently used in the form of a 10% suspension on carbon and is usually present in an amount from about 10 to about 50 weight percent based on the compound of formula II. As will be appreciated by one skilled in the art, Step 1 of Scheme B is a selective hydrogenation, since compound II possesses other reducible groups in addition to the $C_5$-$C_6$ double bond. Accordingly it is necessary to monitor the hydrogen uptake, and to interrupt the hydrogenation when approximately one molecular equivalent of hydrogen has been absorbed. The hydrogenated product is usually recovered simply by removing the catalyst by filtration and then removing the solvent by evaporation in vacuo.

Step 2 of Scheme B involves oxidation of the secondary alcohol at C-9 to an oxo group, and this is carried out in exactly the same manner as discussed earlier for oxidation of compound II to compound III (scheme A). In like manner, Step 3 of Scheme B involves removal of the hydroxy protecting groups, and this is achieved in exactly the same manner as removal of the protecting groups from the compound of formula III (Scheme A).

In one method according to the invention, the compounds of the formula I, wherein $COOR^2$ represents an esterified carboxy group and Z represents a cis double bond, are prepared by first esterifying the carboxy group of a compound of the formula II, to give a compound of the formula VI. The 9-hydroxy group of the compound of the formula VI is then oxidized to a 9-oxo group, and the protecting groups are removed from the hydroxy groups at C-11 and C-15. The oxidation step and the deprotection step are carried out exactly as described previously for operation of Steps 1 and 2 of Scheme A.

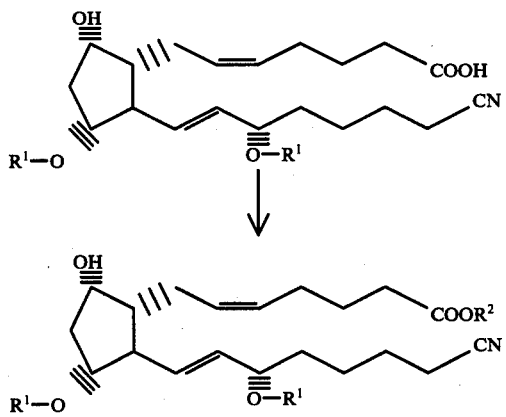

The esterification of a compound of the formula II, to give a compound of the formula VI is carried out using conventional methods known to be appropriate for esterifying prostaglandin compounds. However, a particularly convenient method when $R^2$ is lower-alkyl involves use of the appropriate diazoalkane (e.g. diazomethane, diazoethane, etc.). In this case, a solution of the compound of the formula II in a reaction-inert organic solvent, e.g. ether, is treated dropwise with a solution of approximately one molar equivalent of the diazoalkane in a reaction-inert organic solvent. Esterification takes place rapidly, at or slightly below room temperature, and it is complete within a few minutes. The product is recovered simply by solvent evaporation. 4-Biphenylyl esters are prepared by coupling of an acid of the formula II with 4-phenylphenol in the presence of dicyclohexylcarbodiimide.

In like manner, the compounds of the formula I, wherein $COOR^2$ represents an esterified carboxy group and Z represents a single bond can be prepared from a compound of the formula VI. The compound of formula VI is selectively hydrogenated, the 9-hydroxy group is oxidized to a 9-oxo group, and then the protecting groups are removed from the hydroxy groups at C-11 and C-15, exactly as described for Steps 1, 2 and 3 of Scheme B.

If desired, certain alternate routes can be used to prepare the compounds of this invention wherein $COOR^2$ represents an esterified carboxy group and Z represents a single bond or a cis double bond. Thus, the compounds of the formula I, wherein $COOR^2$ represents an esterified carboxy group and Z represents a cis double bond can be prepared by esterification of the compound of a formula III, followed by removal of the hydroxy protecting groups as described for Step 2 of Scheme A. Additionally, the compounds of the formula I, wherein $COOR^2$ represents an esterified carboxy group and Z represents a cis double bond, can be prepared by direct esterification of the compound of the formula I, wherein $R^2$ is hydrogen and Z represents a cis double bond. In the case of preparing lower-alkyl esters, esterification using a diazoalkane is a particularly convenient technique.

In like manner, the compounds of the formula I, wherein $COOR^2$ represents an esterified carboxy group and Z represents a single bond can be prepared by esterification of the compound of the formula IV, followed by oxidation of the 9-hydroxy group as described for Step 2 of Scheme B and removal of the hydroxy protecting groups as described for Step 3 of Scheme B. Additionally, the compounds of the formula I, wherein $COOR^2$ represents an esterified carboxy group and Z represents a single bond, can be prepared by esterification of the compound of formula V, followed by removal of the hydroxy protecting group as described for Step 3 of Scheme B. Finally, the compound of the formula I, wherein $R^2$ is hydrogen and Z represents a single bond, can be esterified directly, to give a compound of the formula I, wherein $COOR^2$ is an esterified carboxy group and Z represents a single bond. When it is desired to prepare a lower-alkyl ester, esterification using the appropriate diazoalkane is a particularly convenient method.

In a further method according to the invention, the compounds of the formula I, wherein $R^2$ is as defined previously and Z represents a single bond, can be prepared from the corresponding compound in which Z represents a cis double bond, by a three-step procedure which comprises: (a) protection of the C-11 and C-15 hydroxy groups; (b) selective hydrogenation of the $C_5$-$C_6$ double bond at low temperature; and (c) removal of the protecting groups at C-11 and C-15. In this sequence it is necessary to use a protecting group which can be removed by acid, under mild conditions. The 2-tetrahydropyranyl and the 2-tetrahydrofuranyl group can be used for this purpose, and a further group which is particularly convenient is the dimethylisopropylsilyl group. This latter protecting group is introduced, and removed, using standard procedures. The selective hydrogenation of the $C_5$-$C_6$ double bond is performed in the same manner as described earlier for step 1 of Scheme B.

The compounds of the formula II are prepared from 2-[3α-4-phenylbenzoyloxy-5α-hydroxy-2β-formylcyclopent-1α-yl]acetic acid γ-lactone (the compound of formula VII) by the multistep sequence outlined in Scheme C.

SCHEME C

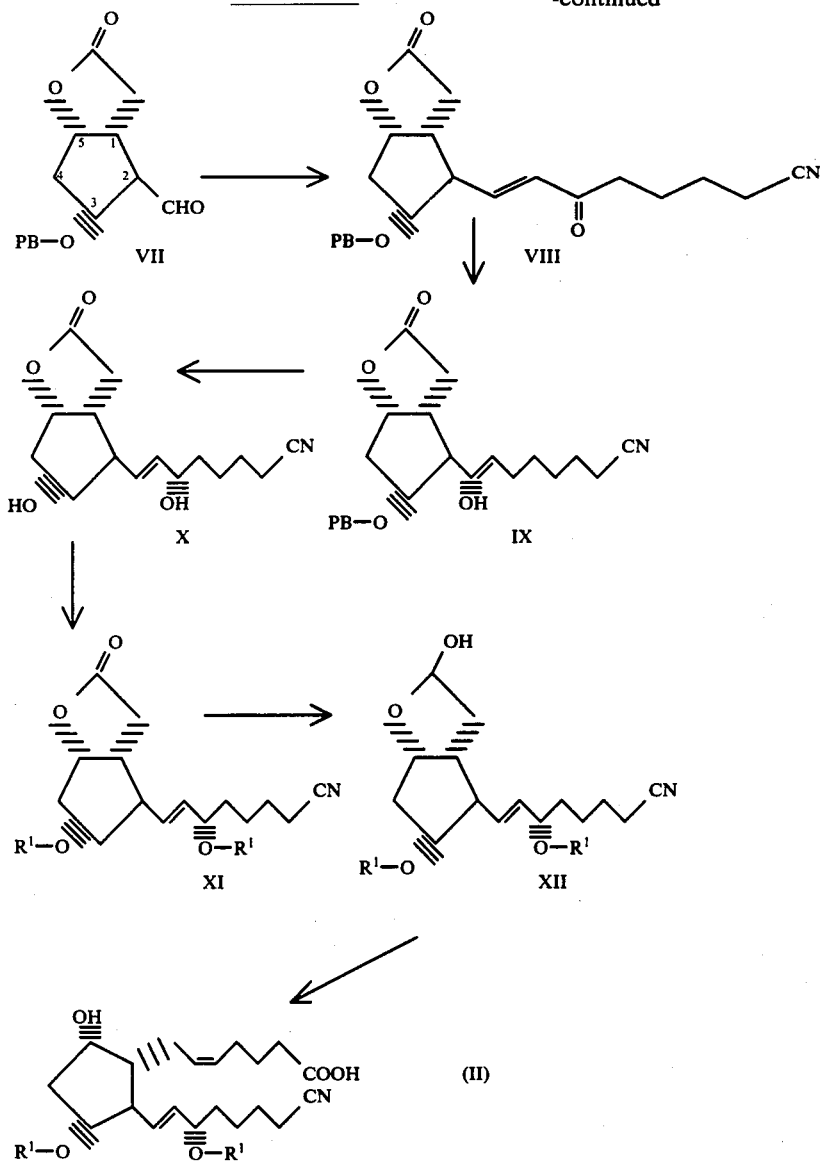

"PB" represents 4-phenylbenzoyl

In the first step of Scheme C, the compound of formula VII is condensed with the anion of dimethyl 2-oxo-6-cyanohexylphosphonate, to give the α,β-unsaturated ketones VIII. Reduction of the compound of the formula VIII with lithium triethylborohydride in tetrahydrofuran gives a mixture of epimers, from which the isomer having the desired stereochemistry (IX) is isolated by column chromatography using silica gel. The desired isomer has the (S)-configuration at C-3 of the 3-hydroxy-7-cyano-1-heptenyl side chain (i.e. the 3-hydroxy group has the α-configuration by prostaglandin stereochemical notation) and it is the less polar of the two isomers. Treatment of the compound of the formula IX with potassium carbonate in methanol removes the 4-phenylbenzoyl group, giving the compound of the formula X. The two secondary alcohol groups are protected, and then the derivative XI is reduced to the hemiacetal XII using diisobutylaluminum hydride. Condensation of the hemiacetal XII with the ylid derived from (4-carboxy-n-butyl)triphenylphosphonium bromide and 2 molar equivalents of sodium methylsulfinylmethide in dimethyl sulfoxide provides the required intermediate II.

2-[3α-4-Phenylbenzoyloxy-5α-hydroxy-2β-formyl-cyclopent-1α-yl]acetic acid γ-lactone (VII) is prepared by the published procedure: *Journal of the American Chemical Society*, 93, 1491 (1971).

As indicated hereinbefore, the compounds of the formula I, wherein $COOR^2$ represents a free or an esterified carboxy group, and Z represents a single bond or a cis double bond are useful as bronchodilatory agents. Accordingly they are useful for controlling bronchial spasm and increasing nasal patency in mammals, particularly man, in such conditions as bronchial asthma, bronchitis, pneumonia and emphysema. For these purposes, these compounds are administered either alone, or, preferably, in combination with pharmaceutically-acceptable carriers or diluents, in accordance with standard pharmaceutical practice for the administration of prostaglandin-type compounds. Thus the bronchodilatory agents of this invention can be administered orally, rectally, parenterally, by inhalation and by insufflation.

For oral use, they are used, for example, in tablets, capsules, solutions or suspensions. For rectal use they are formulated as suppositories. For parenteral use, which includes intramuscular, intraperitoneal, subcutaneous and intravenous administration, sterile solutions of the active ingredient are prepared, with the pH of the solution being adjusted and controlled by the addition of buffering agents. For administration by inhalation the compounds are formulated in aerosols. These aerosols comprise the active ingredient, an inert propellant and a co-solvent, and optionally also contain buffering agents and preservatives. Dry powders containing the active ingredient can be prepared for administration by insufflation.

When the bronchodilatory agents of this invention are used in man the dosage will be selected by the prescribing physician, and it will vary depending on the age, weight and response of the individual patient, as well as the severity of the patient's symptoms and the route of administration. However, in most instances an effective adult dosage will be from 0.01 to about 1.0 mg. per kilogram of body weight per day, in single or divided doses.

The following examples and preparations are provided solely for the purpose of further illustration.

EXAMPLE I

9-Oxo-11α,15α-di(tetrahydropyran-2-yloxy)-19-cyano-20-nor-cis-5-trans-13-prosta-5,13-dienoic Acid To a solution of 800 mg. (1.46 mmole) of 9α-hydroxy-11α,15α-di(tetrahydropyran-2-yloxy)-19-cyano-20-nor-cis-5-trans-13-prosta-5,13-dienoic acid in 8 ml. of acetone, under nitrogen, at −10° C. was added 0.62 ml. of chromic acid (Jones reagent). The reaction mixture was stirred for 30 minutes at −10° C., and then 0.62 ml. of isopropanol was added. After 5 minutes the reaction mixture was diluted with ethyl acetate, and then it was washed with water, dried (MgSO$_4$) and evaporated in vacuo. This afforded 570 mg. of 9-oxo-11α,15α-di(tetrahydropyran-2-yloxy)-19-cyano-20-nor-cis-5-trans-13-prosta-5,13-dienoic acid. The chromic acid used in this experiment was prepared according to the procedure in the *Journal of Organic Chemistry* 21, 1547 (1956).

EXAMPLE II

9-Oxo-11α,15α-dihydroxy-19-cyano-20-nor-cis-5-trans-13-prosta-5,13-dienoic Acid

A solution of 570 mg. of 9-oxo-11α,15α-di(tetrahydropyran-2-yloxy)-19-cyano-20-nor-cis-5-trans-13-prosta-5,13-dienoic acid in 25 ml. of a 65:35 mixture of glacial acetic acid-water was stirred under nitrogen at room temperature for 18 hours, then it was concentrated in vacuo. The resultant crude oil was purified by column chromatography on silica gel (100–200 mesh) using mixtures of chloroform-ethyl acetate as eluents.

After elution of less polar impurities the 9-oxo-11α,15α-dihydroxy-19-cyano-20-nor-cis-5-trans-13-prosta-5,13-dienoic acid was collected as a viscous oil weighing 188 mg. The IR spectrum (CHCl$_3$) of the product exhibited strong absorption bands at 1710 cm$^{-1}$ for the ketone carbonyl and at 1730 cm$^{-1}$ for the acid carbonyl, a medium intensity absorption band at 970 cm$^{-1}$ for the trans double bond, and a weak absorption band at 2235 cm$^{-1}$ for the nitrile.

EXAMPLE III

9-Oxo-11α,15α-di(tetrahydropyran-2-yloxy)-19-cyano-20-nor-trans-prost-13enoic Acid The title compound is prepared by oxidation of 9-hydroxy-11α,15α-di(tetrahydropyran-2-yloxy)-19-cyano-20-nor-trans-prost-13-enoic acid with chromic acid in acetone, using the procedure of Example I.

EXAMPLE IV

9-Oxo-11α,15α-dihydroxy-19-cyano-20-nor-trans-prost-13-enoic Acid

Hydrolysis of 9-oxo-11α,15α-di(tetrahydropyran-2-yloxy)-19-cyano-20-nor-trans-prost-13-enoic acid using aqueous acid, according to the procedure of Example II, affords the title compound.

EXAMPLE V

Methyl 9-oxo-11α,15α-dihydroxy-19-cyano-20-nor-cis-5-trans-13-prosta-5,13-dienoate To a solution of 363 mg. (1 mmole) of 9-oxo-11α,15α-dihydroxy-19-cyano-20-nor-cis-5-trans-13-prosta-5,13-dienoic acid in 10 ml. of ether is added 2 ml. of a 0.5M solution of diazomethane in ether. After 2 minutes, the ethereal solution is washed with sodium carbonate, dried (MgSO$_4$) and evaporated in vacuo to give the title compound.

EXAMPLE VI

Reaction of 9-oxo-11α,15α-dihydroxy-19-cyano-20-nor-cis-5-trans-13-prosta-5,13-dienoic acid with diazoethane, diazopropane and diazobutane, respectively, according to the procedure of Example V, affords:
ethyl 9-oxo-11α,15α-dihydroxy-19-cyano-20-nor-cis-5-trans-13-prosta-5,13-dienoate,
propyl 9-oxo-11α,15α-dihydroxy-19-cyano-20-nor-cis-5-trans-13-prosta-5,13-dienoate and
butyl 9-oxo-11α,15α-dihydroxy-19-cyano-20-nor-cis-5-trans-13-prosta-5,13-dienoate,
respectively.

EXAMPLE VII

Reaction of 9-oxo-11α,15α-dihydroxy-19-cyano-20-nor-trans-prost-13-enoic acid with diazomethane, diazopropane and diazobutane, respectively, according to the procedure of Example V, affords:
methyl 9-oxo-11α,15α-dihydroxy-19-cyano-20-nor-trans-prost-13-enoate,
propyl 9-oxo-11α,15α-dihydroxy-19-cyano-20-nor-trans-prost-13-enoate and
butyl 9-oxo-11α,15α-dihydroxy-19-cyano-20-nor-trans-prost-13-enoate,
respectively.

EXAMPLE VIII

Oxidation of each of the alkyl 9α-hydroxy-11α,15α-di(tetrahydropyran-2-yloxy)-19-cyano-20-nor-cis-5-trans-13-prosta-5,13-dienoates of Preparation I with chromic acid in acetone, according to the procedure of Example I, provides
methyl 9-oxo-11α,15α-di(tetrahydropyran-2-yloxy)-19-cyano-20-nor-cis-5-trans-13-prosta-5,13-dienoate,
ethyl 9-oxo-11α,15α-di(tetrahydropyran-2-yloxy)-19-cyano-20-nor-cis-5-trans-13-prosta-5,13-dienoate and butyl 9-oxo-11α,15α-di(tetrahydropyran-2-yloxy)-19-cyano-20-nor-cis-5-trans-13-prosta,5,13-dienoate, respectively.

EXAMPLE IX

Hydrolysis of each of the alkyl 9-oxo-11α,15α-di(tetrahydropyran-2-yloxy)-19-cyano-20-nor-cis-5-trans-13-prosta-5,13-dienoates of Example VIII with aqueous acetic acid, according to the procedure of Example II, affords:

methyl 9-oxo-11α,15α-dihydroxy-19-cyano-20-nor-cis-5-trans-13-prosta-5,13-dienoate, ethyl 9-oxo-11α,15α-dihydroxy-19-cyano-20-nor-cis-5-trans-13-prosta-5,13-dienoate, and butyl 9-oxo-11α,15α-dihydroxy-19-cyano-20-nor-cis-5-trans-13-prosta-5,13-dienoate, respectively.

EXAMPLE X

Each of the alkyl 9α-hydroxy-11α,15α-di(tetrahydropyran-2-yloxy)-19-cyano-20-nor-cis-5-trans-13-prosta-5,13-dienoates of Preparation I is hydrogenated according to the procedure of Preparation H, and then the product is oxidized with chromic acid in acetone, according to the procedure of Example I. This affords:

methyl 9-oxo-11α,15α-di(tetrahydropyran-2-yloxy)-19-cyano-20-nor-trans-prost-13-enoate, ethyl 9-oxo-11α,15α-di(tetrahydropyran-2-yloxy)-19-cyano-20-nor-trans-prost-13-enoate and butyl 9-oxo-11α,15α-di(tetrahydropyran-2-yloxy)-19-cyano-20-nor-trans-prost-13-enoate, respectively.

EXAMPLE XI

Hydrolysis of each of the alkyl 9-oxo-11α,15α-di(tetrahydropyran-2-yloxy)-19-cyano-20-nor-trans-prost-13-enoates of Example X with aqueous acetic acid, according to the procedure of Example II, affords:

methyl 9-oxo-11α,15α-dihydroxy-19-cyano-20-nor-trans-prost-13-enoate, ethyl 9-oxo-11α,15α-dihydroxy-19-cyano-20-nor-trans-prost-13-enoate and butyl 9-oxo-11,15-dihydroxy-19-cyano-20-nor-trans-prost-13-enoate, respectively.

EXAMPLE XII

4-Biphenylyl 9-Oxo-11α,15α-dihydroxy-19-cyano-20-nor-cis-5-trans-13-prosta-5,13-dienoate To a solution of 109 mg. (0.3 mmole) of 9-oxo-11α,15α-dihydroxy-19-cyano-20-nor-cis-5-trans-13-prosta-5,13-dienoic acid and 510 mg. (3 mmole) of 4-phenylphenol in 10 ml. of dry dichloromethane was added, in two equal portions 30 minutes apart, a total of 3.30 ml. (0.33 mmole) of a 0.1M solution of dicyclohexylcarbodiimide in dichloromethane. The reaction mixture was stirred at ca. 25° C., under nitrogen, overnight, and then the solvent was removed by evaporation in vacuo. The residue was purified by column chromatography on silica gel, which afforded 127 mg. of the title product.

EXAMPLE XIII

Esterification of 9-oxo-11α,15α-dihydroxy-19-cyano-20-nor-trans-prost-13-enoic acid, 9-oxo-11α,15α-di(tetrahydropyran-2-yloxy)-19-cyano-20-nor-cis-5-trans-13-prosta-5,13-dienoic acid and 9-oxo-11α,15α-di(tetrahydropyran-2-yloxy)-19-cyano-20-nor-trans-prost-13-enoic acid, respectively, with 4-phenylphenol, according to the procedure of Example XII, affords the following compounds:

4-biphenylyl 9-oxo-11α,15α-dihydroxy-19-cyano-20-nor-trans-prost-13-enoate, 4-biphenylyl 9-oxo-11α,15α-di(tetrahydropyran-2-yloxy)-19-cyano-20-nor-cis-5-trans-13-prosta-5,13-dienoate, and 4-biphenylyl 9-oxo-11α,15α-di(tetrahydropyran-2-yloxy)-19-cyano-20-nor-trans-prost-13-enoate, respectively.

EXAMPLE XIV

Hydrolysis of 4-biphenylyl 9-oxo-11α,15α-di(tetrahydropyran-2-yloxy)-19-cyano-20-nor-cis-5-trans-13-prosta-5,13-dienoate, according to the procedure of Example II, affords 4-biphenylyl 9-oxo-11α,15α-dihydroxy-19-cyano-20-nor-cis-5-trans-13-prosta-5,13-dienoate.

In like manner, hydrolysis of 4-biphenylyl-9-oxo-11α,15α-di(tetrahydropyran-2-yloxy)-19-cyano-20-nor-trans-prost-13-enoate, according to the procedure of Example II, affords 4-biphenylyl 9-oxo-11α,15α-dihydroxy-19-cyano-20-nor-trans-prost-13-enoate.

PREPARATION A

Dimethyl 2-Oxo-6-cyanohexylphosphonate

To a stirred solution of 33.8 g. (270 mmole) of dimethyl methylphosphonate in 340 ml. of dry tetrahydrofuran, cooled to −78° C., under nitrogen, was added, with stirring 120 ml. of a 2.25 M solution of n-butyllithium in hexane. The temperature was maintained between −78° and −65° C. during the addition. The mixture was stirred for 5 minutes at −78° C., and then 20.9 g. (135 mmole) of ethyl 5-cyanopentanoate was added dropwise during 5 minutes, maintaining the temperature in the range from −78° to −70° C. After 1 hour at −78° C., the reaction mixture was allowed to warm to 25° C., neutralized using 20 ml. of glacial acetic acid and then the volatile components were removed by evaporation in vacuo. The gelatinous residue was dissolved in 50 ml. of water, which was then extracted with methylene chloride. The organic extracts were washed with water, dried (MgSO$_4$) and evaporated to give an oily residue. The residue was distilled, giving 20.6 g. of dimethyl 2-oxo-6-cyanohexylphosphonate, b.p. 146°–62° C. (0.1–0.2 mm). The NMR spectrum of the product (CDCl$_3$) showed absorptions at 3.76 ppm (doublet, J = 11.5 cps, 6H) and 3.18 ppm (doublet, J = 22.5, 2H).

PREPARATION B

2-[3α-(4-Phenylbenzoyloxy)-5α-hydroxy-2β-(3-oxo-7-cyano-trans-1-hepten-1-yl)cyclopent-1α-yl]acetic Acid γ-Lactone To a solution of 14.0 ml. (31.4 mmole) of 2.25 M n-butyllithium in hexane, in 100 ml. of dry tetrahydrofuran, under nitrogen, at ca. 0° C., was added dropwise 8.0 g. (34.3 mmole) of dimethyl 2-oxo-6-cyanohexylphosphonate. The solution was stirred at ca. 0° C. for 10 minutes, and then 10.0 g. (28.6 mmole) of 2-[3α-(4-phenylbenzoyloxy)-5α-hydroxy-2β-formylcyclopent-1α-yl]acetic acid γ-lactone was added. The cooling bath was removed, the mixture was stirred for 1 hour, and then it was quenched with glacial acetic acid to pH 5. The mixture was concentrated in vacuo, and the residue was dissolved in 150 ml. of methylene chloride. The organic phase was washed sequentially with water, saturated sodium bicarbonate and saturated brine, and then it was dried (MgSO₄) and concentrated to a yellow oil. Purification of this crude product by silica gel chromatography using benzene-ethyl acetate as eluents afforded 2-[3α-(4-phenylbenzoyloxy)-5α-hydroxy-2β-(3-oxo-7-cyano-trans-1-hepten-1-yl)-cyclopent-1α-yl]acetic acid, γ-lactone, as a yellow foam weighing 6.00 g. The IR spectrum (CHCl₃) of the product exhibited absorption bands at 1775 cm⁻¹ for the lactone carbonyl, at 1712 cm⁻¹ for the ester carbonyl, 1675 and 1630 cm⁻¹ for the ketone carbonyl, and at 975 cm⁻¹ for the trans double bond.

PREPARATION C

2-[3α-(4-Phenylbenzoyloxy)-5α-hydroxy-2β-(3α-hydroxy-7-cyano-trans-1-hepten-1-yl)cyclopent-1α-yl]acetic Acid γ-Lactone and
2-[3α-(4-phenylbenzoyloxy)-5α-hydroxy-2β-(3β-hydroxy-7-cyano-trans-1-hepten-1-yl)cyclopent-1α-yl]acetic Acid γ-Lactone To a solution, cooled to −45° C. under nitrogen, of 6.0 g. (13.1 mmoles) of 2-[3α-(4-phenybenzoyloxy)-5α-hydroxy-2β-(3-oxo-7-cyano-trans-1-hepten-1-yl)-cyclopent-1α-yl]acetic acid γ-lactone in 130 ml. of dry tetrahydrofuran was added dropwise 13.0 ml. of a 1.0M solution of lithium triethylborohydride in tetrahydrofuran. After being stirred for 45 minutes, the reaction mixture was quenched by the addition of 50 ml. of a 9:1 mixture of water glacial acetic acid. The reaction was allowed to warm to room temperature then the tetrahydrofuran was removed by rotary evaporation. The aqueous layer was extracted with methylene chloride (3 × 100 ml) and the combined organic extracts were dried (anhydrous magnesium sulfate) and concentrated to a white foam. Purification of this crude product by silica gel (60-200 mesh) column chromatography, using mixtures of benzene-ethyl acetate as eluents (250 ml. fractions), afforded 2-[3α-(4-phenylbenzoyloxy)-5α-hydroxy-2β-(3α-hydroxy-7-cyano-trans-1-hepten-1-yl)cyclopent-1α-yl]acetic acid, γ-lactone as a colorless oil weighing 3.40 g. Further elution of the column afforded 2.12 g. of 2-[3α-(4-phenylbenzoyloxy)-5α-hydroxy-2β-(3β-hydroxy-7-cyano-trans-1-hepten-1-yl)cyclopent-1α-yl)acetic acid γ-lactone as a viscous oil. The IR spectra of each of the two products showed absorption bands at 1775 cm⁻¹ for the lactone carbonyl, at 1715 cm⁻¹ for the ester carbonyl, and 965 cm⁻¹ for the trans double bond.

PREPARATION D

2-[3α,5α-Dihydroxy-2β-(3α-hydroxy-7-cyano-trans-1-hepten-1-yl]cyclopent-1α-yl]acetic Acid γ-lactone A heterogeneous mixture of 3.40 g. (7.42 mmole) of 2-[3α-(4-phenylbenzoyloxy)-5α-hydroxy-2β-(3α-hydroxy-7-cyano-trans-1-hepten-1-yl)cyclopent-1α-yl]acetic acid γ-lactone, 34 ml. of absolute methanol and 1.28 g. of finely powdered, anhydrous potassium carbonate was stirred at room temperature for 1.5 hour, and then it was cooled to 0° C. To the cooled solution was added 18.5 ml. of 1.0N aqueous hydrochloric acid. After stirring at 0° C. for an additional 10 minutes, 34 ml. of water was added and the methyl 4-phenylbenzoate which precipitated was collected by filtration. The filtrate was concentrated by evaporation in vacuo and then it was extracted with ethyl acetate (3×). The combined organic extracts were dried (MgSO₄), and concentrated, to give 1.27 g. of 2-[3α,5α-dihydroxy-2β-(3α-hydroxy-7-cyano-trans-1-hepten-1-yl)cyclopent-1α-yl]acetic acid γ-lactone as an oil. The IR spectrum (CHCl₃) exhibited a strong adsorption band at 1775 cm⁻¹ for the lactone carbonyl, a medium adsorption at 975 cm⁻¹ for the trans double bond, and a weak absorption at 2230 cm⁻¹ for the nitrile.

PREPARATION E

2-[5α-Hydroxy-3α-(tetrahydropyran-2-yloxy)-2β-(3α-[tetrahydropyran-2-yloxy]-7-cyano-trans-1-hepten-1-yl)cyclopent-1α-yl]acetic Acid γ-Lactone To a solution of 1.27 g. (4.66 mmole) 2-[3α,5α-dihydroxy-2β-(3α-hydroxy-7-cyano-trans-1-hepten-1-yl)cyclopent-1α-yl]acetic acid, γ-lactone, in 13 ml. anhydrous methylene chloride and 1.3 ml. of 2,3-dihydropyran, at 0° C., in a dry nitrogen atmosphere, was added a few crystals of 4-toluenesulfonic acid monohydrate. After stirring for 15 minutes the reaction mixture was combined with 130 ml ether. The ether solution was washed with saturated sodium bicarbonate (1 × 30 ml) then saturated brine (1 × 15 ml), dried (MgSO₄), and concentrated in vacuo to yield 2.21 g. of crude 2-[5α-hydroxy-3α-(tetrahydropyran-2-yloxy)-2β-(3α-[tetrahydropyran-2-yloxy]-7-cyano-trans-1-hepten-1-yl)-cyclopent-1α-yl]acetic acid γ-lactone which was used without purification.

PREPARATION F

2-[5α-Hydroxy-3α-(tetrahydropyran-2-yloxy)-2β-(3α-[tetrahydropyran-2-yloxy]-7-cyano-trans-1-hepten-1-yl)cyclopent-1α-yl]acetaldehyde γ-Hemitacetal A solution of 2.29 g (4.91 mmole) 2-[5α-hydroxy-3α-(tetrahydropyran-2-yloxy)-2β-(3α-[tetrahydropyran-2-yloxy]-7-cyano-trans-1-hepten-1-yl)cyclopent-1α-yl]acetic acid γ-lactone in 25 ml dry toluene was cooled to −78° C. under dry nitrogen. To this cooled solution was added 6.1 ml. of a 20% solution of diisobutylaluminum hydride in n-hexane, dropwise, at such a rate that the internal temperature did not rise above −65° C. (15 minutes). After an additional 60 minutes of stirring at −78° C., anhydrous methanol was added until gas evolution ceased. The reaction mixture was allowed to warm to room temperature and then it was concentrated in vacuo. The resultant oil was stirred under methanol, and the aluminum salts were removed by filtration. Concentration of the filtrate afforded the crude product which was purified by silica gel (60–200 mesh) column chromatography, eluting with mixtures of benzene-ethyl acetate. After removal of less polar impurities, 2-[5α-hydroxy-3α-(tetrahydropyran-2-yloxy)-2β-(3α-[tetrahydropyran-2-yloxy]-7-cyano-trans-1-hepten-1-yl)cyclopent-1α-yl]acetaldehyde γ-hemiacetal was obtained as a viscous oil weighing 1.79 g. The IR spectrum (CHCl₃) of the purified product exhibited a medium intensity absorption band at 975 cm⁻¹ for the trans double bond and no absorption in the carbonyl region of the spectrum.

PREPARATION G

9α-Hydroxy-11α,15α-di(tetrahydropyran-2-yloxy)-19-cyano-20-nor-cis-5-trans-13-prosta-5,13-dienoic Acid To a solution of 5.31 g. (12.0 mmole) of (4-carboxy-n-butyl)triphenylphosphonium bromide under a dry nitrogen atmosphere in 12 ml. dry dimethyl sulfoxide was added 13.4 ml (23.5 mmole) of a 1.76M solution of sodium methylsulfinylmethide in dimethyl sulfoxide. To this red ylide solution was added dropwise a solution of 1.79 g. (4.0 mmole) 2-[5α-hydroxy-3α-(tetrahydropyran-2-yloxy)-2β-(3α-[tetrahydropyran-2-yloxy]-7-cyano-trans-1-hepten-1-yl)cyclopent-1α-yl]acetaldehyde γ-hemiacetal in 5.0 ml dry dimethyl sulfoxide, over a period of 20 minutes. After an additional 1.0 hour stirring at room temperature, the reaction mixture was poured onto ice water. The basic aqueous solution was acidified to pH ~3 with 10% aqueous hydrochloric acid. The acidic solution was extracted with ethyl acetate (3×) and the combined organic extracts were washed with water (2×), dried (MgSO$_4$) and evaporated to give a solid residue. This solid residue was purified by silica gel chromatography using chloroform-ethyl acetate as eluents to provide 1.31 g of 9α-hydroxy-11α,15α-di-(tetrahydropyran-2-yloxy)-19-cyano-20-nor-cis-5-trans-13-prosta-5,13-dienoic acid. The IR spectrum (CHCl$_3$) of the purified product exhibited a strong absorption band at 1710 cm$^{-1}$ for the acid carbonyl, a medium intensity absorption band at 970 cm$^{-1}$ for the trans double bond, and a weak absorption band at 2230 cm$^{-1}$ for the nitrile.

PREPARATION H

9α-Hydroxy-11α,15α-di(tetrahydropyran-2-yloxy)-19-cyano-20-nor-trans-prost-13-enoic Acid A suspension of 200 mg. of 10% palladium-on-carbon in 30 ml of ethanol is stirred under an atmosphere of hydrogen, at atmospheric pressure and at −20° C., until hydrogen uptake ceases. A solution of 1.0 g. of 9α-hydroxy-11α,15α-di(tetrahydropyran-2-yloxy)-19-cyano-20-nor-cis-5-trans-13-prosta-5,13-dienoic acid in 5 ml. of ethanol is then added at −20° C., and the hydrogenation is continued at −20° C. until one molar equivalent of hydrogen has been absorbed. The filtered reaction mixture is evaporated in vacuo to give the title compound.

PREPARATION I

Reaction of 9α-hydroxy-11α,15α-di(tetrahydropyran-2-yloxy)-19-cyano-20-nor-cis-5-trans-13-prosta-5,13-dienoic acid with diazomethane, diazoethane and diazobutane, respectively, according to the procedure of Example V, affords:

methyl 9α-hydroxy-11α,15α-di(tetrahydropyran-2-yloxy)-19-cyano-20-nor-cis-5-trans-13-prosta-5,13-dienoate, ethyl 9α-hydroxy-11α,15α-di(tetrahydropyran-2-yloxy)-19-cyano-20-nor-cis-5-trans-13-prosta-5,13-dienoate, butyl 9α-hydroxy-11α,15α-di(tetrahydropyran-2-yloxy)-19-cyano-20-nor-cis-5-trans-13-prosta-5,13-dienoate, respectively.

What is claimed is:

1. A compound of the formula

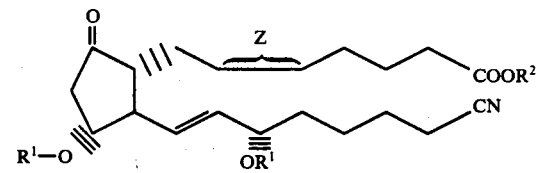

wherein

R$^1$ is 2-tetrahydropyranyl;

R$^2$ is selected from the group consisting of hydrogen, alkyl having from one to four carbon atoms and 4-biphenylyl;

and Z represents a single bond or a cis double bond.

2. A compound according to claim 1, wherein R$^2$ is hydrogen.

3. The compound according to claim 2, wherein Z represents a cis double bond.

* * * * *